United States Patent [19]
Mao et al.

[11] Patent Number: 5,688,459
[45] Date of Patent: Nov. 18, 1997

[54] PROCESS FOR PREPARING HIGH WATER-CONTAINING ELASTOMER MEDICAL CATHETER

[75] Inventors: Lijiang Mao; Yuanjie Hu; Dongxu Piao, all of Beijing, China

[73] Assignee: Chin Rehabilitation Research Center, Beijing, China

[21] Appl. No.: 445,024

[22] Filed: May 19, 1995

[30] Foreign Application Priority Data

Aug. 30, 1994 [CN] China ................... 94115612.5

[51] Int. Cl.$^6$ ............................................. B29C 39/02
[52] U.S. Cl. ................... 264/233; 264/300; 264/331.15
[58] Field of Search ........................ 264/233, 300, 264/130, 185, 209.1, 331.15

[56] References Cited

U.S. PATENT DOCUMENTS

| | | | |
|---|---|---|---|
| 3,066,999 | 12/1962 | Nakajo et al. | 264/300 |
| 3,607,812 | 9/1971 | Takigawa et al. | 264/185 |
| 4,005,166 | 1/1977 | Quick | 264/154 |
| 4,642,267 | 2/1987 | Creasey et al. | 428/413 |
| 4,765,937 | 8/1988 | Hyon et al. | |
| 4,851,168 | 7/1989 | Graiver et al. | 524/379 |
| 4,906,237 | 3/1990 | Johansson et al. | 604/265 |
| 5,061,424 | 10/1991 | Karimi et al. | 264/130 |
| 5,160,790 | 11/1992 | Elton . | |
| 5,225,120 | 7/1993 | Graiver et al. | 264/185 |
| 5,358,677 | 10/1994 | Muth et al. | 264/185 |
| 5,422,050 | 6/1995 | Graiver et al. | 524/503 |

FOREIGN PATENT DOCUMENTS 64-77616  3/1989  Japan ................... 264/185

*Primary Examiner*—Jeffery R. Thurlow
*Attorney, Agent, or Firm*—McAulay Fisher Nissen Goldberg & Kiel, LLP

[57] ABSTRACT

The present invention provides a process for preparing a high water-containing elastomer medical catheter and a urinary catheter prepared by the process. The process is carried out by a) heating a mixture consisting of polyvinyl alcohol, water, sulfoxide and linear alkane, in a sealed vessel with agitating; b) pouring the resulting homogeneous fluid into a mould; c) solidifying the fluid by cooling; d) releasing the solidified fluid from the mould; and e) heat-treating the resulting medical catheter and washing with a polar organic solvent. The medical catheter and the urinary catheter of the present invention have excellent lubricity.

13 Claims, 1 Drawing Sheet

PROCESS FOR PREPARING HIGH WATER-CONTAINING ELASTOMER MEDICAL CATHETER

BACKGROUND OF THE INVENTION

The present invention relates to a high water-containing elastomer medical catheter, especially urinary catheter and to a process for preparing the same.

It has long been a clinical practice that medical catheter, especially urinary catheter, is made of hydrophobic polymeric materials such as rubber and plastics. The poor surface lubricity of the catheter often causes pains and sufferings due to contact and friction upon insertion into the body cavity. In addition to its high tendency of damaging the mucosal tissue, it may also bring about cross infection which may jeopardize the life of the patient. In order to improve its surface lubricity, the surface is usually overcoated with lubricant, which may not only lead to inconvenience to catheterization but also remain some of lubricants inside the body. This is detrimental to the health of the people, too.

In recent years, a wide variety of methods has been put forward and tried in order to reduce surface friction and provide excellent lubricity to the catheter, which is generally formed of a layer onto the surface of the conventional material with a hydrophilic polymer. For example, the method disclosed in U.S. Pat. No. 4,642,267, uses a simple blend of thermoplastic polyurethane and polyvinyl pyrrolidone (PVP) depositing onto the surface of the catheters. This coated layer does not adhere firmly to the plastic substrate, and it is easy to be stripped off when contacting water, physiological saline, urine or other body fluid worsening its surface lubricity. U.S. Pat. No. 5,160,790 proposes a new method in order to overcome the defects. The catheter made of polyurethane is dipped into a mixture of isocyanate, polyethylene glycol, PVP and halogenated hydrocarbon. After removing the solvent by evaporation and applying some other post-treatments, a catheter having hydrogel-coated surface is obtained, which has lasting lubricity when wetted with water. However, a major defect of the method is that in order to meet the needs of fluidity (low viscosity) during the coating process, a large amount of solvents which can dissolve all the components but do not react with any of them is needed. At present stage, the proper solvent to meet the needs can only be a low-boiling halogenated hydrocarbon, such as chloromethane, dibromomethane, chloroform, and dichloroethane. All these solvents are inflammable and poisonous, which must be recovered under strict conditions. This will add to the burden of safety and environment and also increase the production cost.

It is taught in other prior art that onto the surface of the catheter is graft-polymerized hydrophilic monomers by using low temperature plasma or irradiation. Even though these methods have overcome the problems of stripping of the hydrophilic coating, the technological process is generally long and the work is rather complicated, which is not helpful for lowering the production cost and construction investment. In addition, in a wide variety of literatures, high water-containing elastomer and high strength polyvinyl alcohol hydrogel and the production technique of the shaped articles have been described, such as the technique of vacuum dehydration (Japanese Kokai Patent SHOWA 57-13053, SHOWA 58-36630), the technique of repeated freezing [M. Nambu, Polymer Applications (Japan), 32,523 (1983)], the technique of slow-thawing [S. H. Hyon, Y. Ikada, Report of the Poval Committee, No. 8391 (1983)] and the technique of gel spinning (Japanese Kokai Patent SHOWA 59-130314). However, up to the present day, no other prior art similar or close to the present invention in terms of the purpose of invention, technology, and use of product has been found.

Therefore, what is thirstily desired for is a medical catheter, especially urinary catheter, having excellent lubricity and readily available at a lower price.

SUMMARY OF THE INVENTION

Through a long period of intensive research, the present inventors have found a method for preparing a high water-containing elastomer medical catheter with polyvinyl alcohol, water, sulfoxide and linear alkane containing 10–55 carbon atoms and thereby medical catheters, especially urinary catheters are made.

Figure 1:
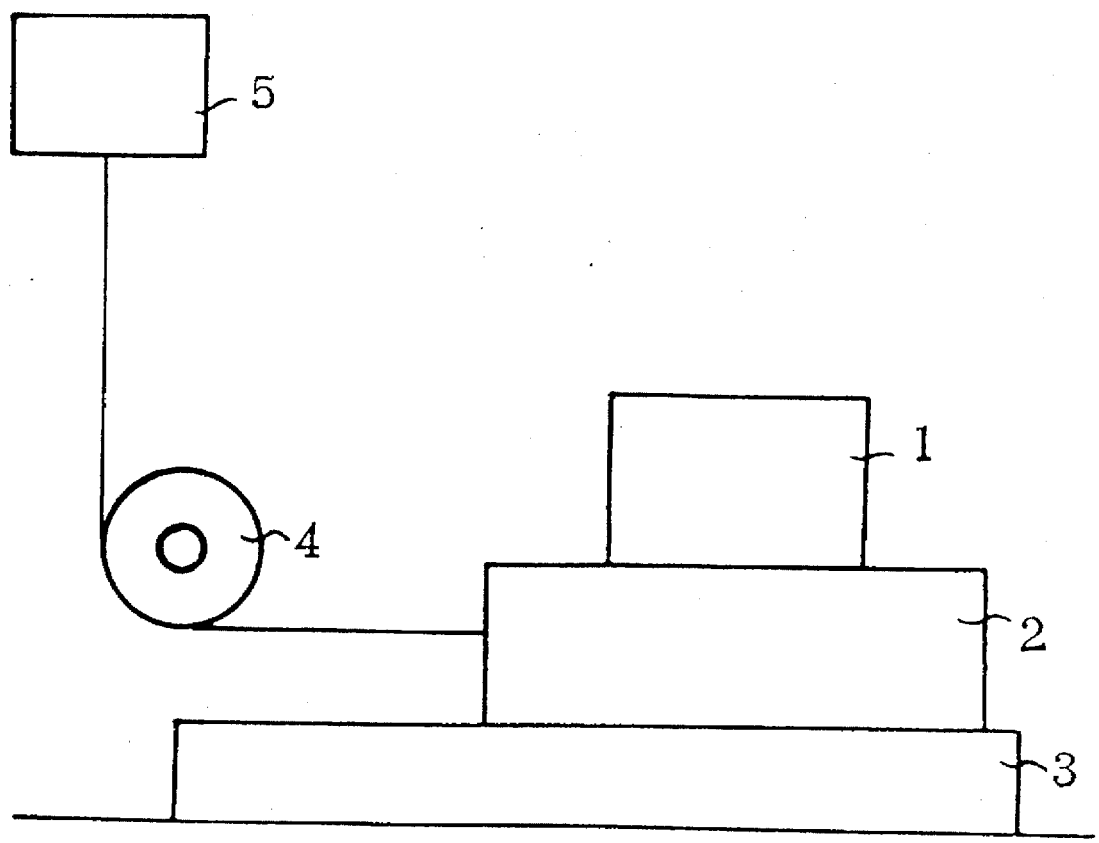
FIG. 1 is a schematic drawing of the measurement of relative friction coefficient of a urinary catheter.

Thus it is an object of the present invention to provide a process for preparing a high water-containing elastomer medical catheter and medical catheters, especially urinary catheters produced by the process.

More particularly, the present invention relates to a process for preparing a high water-containing elastomer medical catheter comprising the steps of:

a) heating a mixture consisting of 20–40 wt % of polyvinyl alcohol, 40–60 wt % of water, 7–15 wt % of sulfoxide having the following general formula

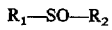

wherein $R_1$ and $R_2$ individually represent alkyl containing 1–3 carbon atoms, and 2–10 wt % of linear alkane containing 10–55 carbon atoms, based on the total weight of the mixture, in a sealed vessel with agitating to form a homogeneous fluid;

b) pouring said homogeneous fluid into a mould having desired shape;

c) solidifying said fluid by cooling;

d) releasing the solidified fluid from the mould to obtain a shaped medical catheter; and e) heat-treating said shaped catheter and then washing with a polar organic solvent.

The present invention also relates to a medical catheter, especially urinary catheter produced by the above process. The medical catheter, especially urinary catheter according to the present invention has excellent lubricity meeting the needs of clinical practice.

Surface lubricity of a catheter mentioned in the prior art was measured when wetted with water. Nothing has ever been mentioned regarding performance attenuation of a catheter when exposed to atmosphere. However, this is a practical problem in clinical practice. The term "excellent lubricity" used herein means that lubricity of a wetted catheter will not attenuate after exposed to atmosphere for 20 minutes. The self-lubrication durability of the catheter of the present invention can fully meet the needs of clinical practice.

The polyvinyl alcohol used in the present invention is actually a random copolymer of vinyl alcohol-vinyl acetate having an average degree of polymerization ranging from 500 to 20,000, preferably 1,500 to 2,500, and a mole percentage of the vinyl alcohol unit (hereinafter referred to as degree of hydrolysis) of above 95 mol %, preferably above 99.5 mol %. If the average degree of polymerization of polyvinyl alcohol is lower than 500, the mechanical properties of the shaped article cannot be guaranteed. When the average degree of polymerization is higher than 20,000, the technological requirements would be too hard to meet.

The polyvinyl alcohol used in the present invention can be made in accordance with the known process in the art or can be purchased at the market.

The sulfoxide used in the present invention is those having the following formula:

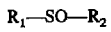

wherein $R_1$ and $R_2$ individually represent $C_1$–$C_3$ alkyl e.g. methyl, ethyl and propyl. The preferable sulfoxide is dimethyl sulfoxide, diethyl sulfoxide, methyl ethyl sulfoxide or their mixtures.

The $C_{10}$–$C_{55}$ linear alkane used in the present invention refers to petroleum wax, including atoleine (having 10–18 carbon atoms, an average molecular weight betw. 150 and 250 and a melting point lower than 27° C.), paraffin wax (having 18–30 carbon atoms, an average molecular weight betw. 250 and 450 and a melting point lower than 27° C.–67° C.), ozocerite (having 30–55 carbon atoms, an average molecular weight above 450 and a melting point betw. 67° C. and 87° C.). The above three petroleum wax products can be used in combination at any ratio or a particular fraction of a petroleum wax product alone. Generally any kind of linear alkane can be used so long as it is readily melted at a higher temperature and condensed or solidified at normal temperature. However, atoleine is more advantageous to the surface lubricity of the shaped articles. Any petroleum wax used should be of a high degree product in view of medical uses; for example, medical grade atoleine and all refined paraffin wax were employed in the present invention.

The petroleum wax used in the present invention can be made in accordance with the known process in the art or can be purchased at the market.

The polar organic solvent used in the present invention should be fully miscible with sulfoxide and water, and immiscible with linear alkane and polyvinyl alcohol. This sort of polar solvent refers to lower alcohols, such as methanol, ethanol, propanol and butanol; aliphatic ketone having 3 or 4 carbon atoms, such as acetone and methyl ethyl ketone; the mixtures of the above alcohols and ketones, and their aqueous solutions.

The specific ratios of the components in the mixture vary upon the degree of hydrolysis, degree of polymerization of polyvinyl alcohol, shape, size and required mechanical properties of the shaped article, etc. When preparing a thin wall tubular article, polyvinyl alcohol with higher degree of hydrolysis and polymerization should be used and the proportion thereof should be correspondingly increased.

The mixture formulated is heated and agitated usually at a temperature between 95° C. and 135° C. for 3–8 hours to dissolve the solid component and then kept at that temperature for 5–20 hours until a homogeneous fluid is formed. The specific condition of dissolution depends on the factors, such as the total weight of the mixture, concentration of polyvinyl alcohol and others.

For example, the heating time should be increased when the amount of starting materials is increased; and the temperature should be raised when the concentration of polyvinyl alcohol is increased. The operation of dissolution is preferably to be performed in a sealed metal vessl equipped with an agitator.

The resulting homogeneous fluid was poured into a mould, cooled to the room temperature (for example 20° C.–30° C.) for solidification, and the shaped article was then released from the mould. The time of cooling depends on the size and shape of the shaped article and the cooling temperature. The shaped articles according to the present invention can be released readily.

The mould can be made in accordance with the type of the shaped article in need.

After released, the shaped article or medical catheter was proceessed by heat treatment at a temperature of 90° C.–110° C. for a period of time, for example 15–45 minutes, and was then washed one or more times with polar organic solvent mentioned as above until no sulfoxide can be detected in the washed solution.

Medical catheter or urinary catheter thus prepared should be sterilized by carefully selecting the sterilizing method. When γ-radiation sterilization is used, breakage of macromolecule may occur, resulting in sharp decrease of mechanical property if radiation condition is improper. When high temperature sterilization is conducted in a high water-containing situation, it may lead to thawing of the elastomers. The inventors have proved through their study that pharmaceutic sterilization would be the best choice for sterilizing the medical catheter of the present invention in addition to other conventional sterilizing methods such as gas (ethylene oxide) sterilization, dry heat sterilization and high pressure steam sterilization. The operation of pharmaceutic sterilization is so simple that what is needed is only to immerse the shaped article in an aqueous solution of bromogeramine or hibitane at ambient temperature. After sterilization, the medical catheters (e.g. urinary catheter) can be sealed in polyethylene packing bag containing sterilizing, liquid for storage. This sort of package is quite convenient to people (for example, the aged and disabled) for self-treatment at home.

In accordance with the process of the present invention any shape and size of the articles can be moulded if desired. In the case of film or sheet, a thickness of $10^{-2}$–10 mm may be employed. In the case of rod and tube, the shape of cross section may be optional. In the case of rod with round cross section, an average cross section diameter of above 0.1 mm is employed. The tubular articles used for medical purpose mainly refer to various medical catheters which often have an average external diameter of 0.5–20 mm and a wall thickness of 0.1–9 min. The urinary catheter generally has an average external diameter of 3–8 mm and a wall thickness of 1–3 min. When used for medical purpose, a spheroid article, usually having an external diameter of 5–100 mm, is often jointed with one or more tubes. According to the present invention, the spheroid and tube (s) can be moulded in integrity or the spheroid and the tube can be jointed together after they have been made respectively.

The shaped article according to the present invention e.g. the medical catheter, especially urinary catheter, has a tensile strength of above 0.3 Kgf/mm$^2$, a breaking elongation of 200–4,000 g, and Young's modulus of no less than 0.08 Kgf/mm$^2$.

The medical catheter of the present invention has surface lubricity which meets the requirements in clinical practice.

The lubricity of the medical catheter according to the present invention can be evaluated in two ways.

1) measurement of relative friction coefficient

The meansuring apparatus is shown in FIG. 1. On the fixed urinary catheter (3) is placed a piece of smooth-surfaced polyvinyl alcohol hydrogel (2) containing 70 wt % of water and a weight (1) is loaded on. Said hydrogel (2) is connected to the load cell (5) of a universal tensile tester with a nylon wire which is pre-embedded into the hydrogel (2) through a pulley (4) with low frictional resistance. By starting the tester, the relative friction coefficient is measured.

Experiment conditions: The experiment is carried out under open air so as to simulate the actual situation. The sample (e.g. the urinary catheter) is tested after exposed to the air for ten minutes. The value measured is a relative friction coefficient value between the surface of urinary catheter and the surface of polyvinyl alcohol hydrogel.

The experiment is carried out with a universal tensile tester of the type SHIMAZU AG 500A, made in Japan.

(2) Clinical trial (20-30 male adult patients as subject).

The results of the two experiments show that the present invention provides a urinary catheter with its surface lubricity considerably superior to that of the urinary catheter made from pure polyvinyl alcohol hydrogel.

The relative friciction coefficient of the medical catheter according to the present invention is less than 0.08 after it was wetted with water or physiological saline and exposed to atmosphere (RH65%, 25° C.) for ten minutes.

The medical catheter according to the present invention shows a remarkable self-lubricity when used in practice. Even though it is not limited by any of theories, it is believed that the durable surface lubricity may result from the synergistic effect of: (1) the unique formulation and process efficiently restrain evaporation of water and keep the material surface in a high water-containing state, and (2) linear alkane and water in the material remain in a stable coexisting state, and play a role of lubrication.

The invention is further illustrated by the following non-limiting examples:

EXAMPLE 1

A stainless vessel was charged with 150 g of polyvinyl alcohol with an average degree of polymerization of 1,750 and a degree of hydrolysis of 99.95 mol % (product of Beijing Organic Chemical Company, Beijing, China), 252 g of distilled water, 70 g of dimethyl sulfoxide and 28 g of atoleine. The mixture was heated gradually to 110° C. with agitating and then maintained at that temperature for 15 hours to form a homogeneous fluid. The hot fluid was poured into a common urinary catheter mould and then cooled to the room temperature to solidify the fluid. After released, the urinary catheter was heat-treated at 105° C. for 40 minutes, and washed sequentially three times with 50 wt %, 75 wt % and 95% aqueous solutions of ethanol in bath ratios 1:5, 1:8 and 1:10 for 20 minutes respectively. The washed urinary catheter was immersed in normal saline containing 0.1% of hibitane for 2 hours, then sealed in a medical plastic bag holding 0.1% aqueous solution of hibitane.

The resulting urinary catheter having a perimeter (Fr) of 14 mm possesses a tensile strength of 0.36 Kgf/mm$^2$, breaking elongation of 3500%, Young's modulus of 0.1 Kgf/mm$^2$ and relative friction coefficient of 0.077.

The results of the clinical trials on subjects of 30 male adult patients (the urinary cathter used was directly from the sealed plastic bag without coating any lubricant) showed there was no resistance when the urinary catheter was inserted into and pulled out of the urethra and the urine flew out smoothly. The patient did not have any sensation of pain, only with very vague and bearable foreign body sensation. The urinary catheter remained inside the urethras of five patients for 3 to 7 days. The clinical observation shows that the ureteral secretion due to rejection of foreign body was considerably less than the secretion resulted from using other types of urinary catheters. After the ureteral catheterization, the shape of the catheter did not change and its mechanical property remained the same as usual.

EXAMPLE 2

A stainless vessel was charged with 110 g of polyvinyl alcohol with an average degree of polymerization of 7,000 and a degree of hydrolysis of 99. 5 mol % (product of KURARY Corporation, Japan), 290 g of distilled water, 75 g of dimethyl sulfoxide and 25 g of atoleine. The mixture was heated gradually to 130° C., with agitating and then kept at that temperature for 8 hours. The hot solution was poured into a mould of common urinary catheter and then cooled to the room temperature till the solution was solidified. The other procedures of treatment are the same as those described in Example 1.

The resulting urinary catheter having a perimeter (Fr) of 14 mm possesses a tensile strength of 0.54 Kgf/mm$^2$, breaking elongation 1500%, Young's modulus of 0.14 Kgf/mm$^2$ and relative friction coeffcient of 0.069.

The results of the clinical trials on subjects of 10 male adult patients showed there was no resistance when the urinary catheter was inserted into and pulled out of the urethra and the urine flew out smoothly. The patients did not have any sensation of pain, only with very vague and bearable foreign body sensation. The urinary catheter remained inside the urethras of two patients for 5 days. The clinical observation showed that the ureteral secretion due to rejection of foreign body was considerably less than the secretion resulted from using other types of urinary catheters. After the ureteral catheterization, the shape of the catheter did not change and its mechanical property remained the same as usual.

EXAMPLE 3

The procedures of Example 1 were repeated except the replacement of 70 grams of dimethyl sulfoxide with 65 grams of diethyl sulfoxide (chemical reagent of AR Grade, product of NAKARAI Chemical Reagent Corporation, Japan).

The resulting urinary catheter having a length of 400 mm and a diameter of 5.2 mm possesses a tensile strength of 0.34 Kgf/mm$^2$, breaking elongation of 3,000%, Young's modulus of 0.11 Kgf/mm$^2$ and relative friction coefficient of 0.078.

The results of the clinical trials on 10 male adult patients are the same as those described in Example 2.

EXAMPLE 4

The procedures of Example 1 were repeated except the replacement of 28 g of atoleine with 25 g of a mixture of ozocerite-paraffin wax (weight ratio 1:5).

The resulting urinary catheter having a length of 400 mm and a diameter of 5.2 mm possesses a tensile strength of 0.35 Kgf/mm$^2$, breaking elongation of 3,000%, Young's modulus of 0.11 Kgf/mm$^2$ and relative friction coefficient of 0.071.

The results of the clinical trials on 10 male adult patients are the same as those described in Example 2.

COMPARATIVE EXAMPLE 1

The urinary catheters of polyvinyl chloride (made in Shanghai, China, Fr=14, available in the market) were coated with atoleine (M. G. product by Fushun Medicine Company, Fushun, China). The disposable coated catheters were tested in the clinical trials on 20 male adult patients.

Before inserting the catheter into the urethra, 3 ml of atoleine was injected into the urethra for prevention of mucosal damage and reduction of pain. Consequently, there was a little resistance and the passage was rather smooth when the catheter was inserted into and pulled out of the urethra. All the patients had a sensation of foreign body and slight pain.

The urinary catheter of polyvinyl chloride has a relative friction coefficient of 0.09 when it is coated with lubricant (atoleine). The relative friction coefficient is 1.90 without being coated with lubricant, which cannot be used in clinical practice.

Note: Fr stands for the perimeter (mm) of the urinary catheter.

COMPARATIVE EXAMPLE 2

The silicone catheters (made in Shanghai, China, Fr=14, available in the market) coated with ZHITONGJIAO (a lubricant containing 1% of cocaine hydrochloride and an appropriate amount of germicide, produced by the First Brach of Xi'an Medicine Company, Xi'an, China) were used for clinical trails as disposable on 20 male adult patients. Before inserting the catheter into the urethra, 3 ml of lubricant ZHITONGJIAO was injected into the urethra for prevention of mucosal damage and reduction of pain. Consequently, there was little resistance and the passage was quite smooth when the catheter was inserted into and pulled out of the urethra. All the patients did not feel painful except for a slight sensation of foreign body.

The silicone catheter coated with lubricant has a relative friction coefficient of 0.08. The value is 2.00 when the catheter is not coated with lubricant, which cannot be used in clinical practice.

COMPARATIVE EXAMPLE 3

(Direct use of the catheter after seal destruction without coating with lubricant)

A stainless vessel was charged with 30 g of polyvinyl alcohol with an average degree of polymerization of 1750 and a degree of hydrolysis of 99.95 mol % and 70 g of distilled water. The mixture was agitated at the room temperature for 30 minutes and then heated gradually to a temperature of 110° C. with agitating, and then kept at that temperature for 1 hour. The hot solution was poured into a mould of common urinary catheter, cooled to the room temperature and then put into a freezer with a temperature of −12° C. for 3 hours and then put into cold cabinet with a temperature of 5° C. for ten hours for slow thawing. The resulting urinary catheter was sterilized and packed in the manner as described in Example 1. The resulting urinary catheter has a tensile strength of 0.2 Kgf/mm², breaking elongation of 400%, Young's modulus of 0.07 Kgf/mm² and relative friction coefficient of 0.1.

The results of the clinical trial on 5 male adult patients showed that when the urinary catheter was exposed to atmosphere, the water on its surface evaporated quickly. There was a large resistance when the catheter was inserted into the urethra, with the pains beyond the patient's bearing. The catheter could not be inserted into the urinary bladder for catheterization.

COMPARATIVE EXAMPLE 4

(Direct use of the catheter after seal destruction without coating with lubricant)

Example 1 was repeated except that the Linear alkane (atoleine) was not used. The resulting urinary catheter has a tensile strength of 0.3 Kgf/mm², breaking elongation of 2,000%, Young's modulus of 0.2 Kgf/mm² and relative friction coefficient of 0.1.

The results of the clinical trims on 5 male adult patients showed that there was some resistance and hindrance when the urinary catheter was inserted into the urethra but it could reach the urinary bladder for catheterization. It was hard to pull the catheter out of the urethra as if it was "sucked" by the urethra. The catheter showed a permanent deformation when it was drawn out.

COMPARATIVE EXAMPLE 5

Example 1 was repeated except that polyvinyl alcohol with a degree of hydrolysis of 88.0 mol % was used. The resulting urinary catheter has a tensile strength of 0.03 Kgf/mm², breaking elongation of 150%, Young's modulus of 0.12 Kgf/mm².

The clinical trial could not be carried out because the mechanical property of the urinary catheter did not meet the requirement.

While the invention has been described in detail and with reference to specific embodiments thereof, it will be apparent that various changes and modifications can be made therein without departing from the spirit and scope thereof.

What is claimed is:

1. A process for preparing a high water-containing elstomer medical catheter comprising the steps of:
   a) heating a mixture consisting of 20–40 wt % of polyvinyl alcohol, 40–60 wt % of water, 7–15 wt % of sulfoxide having the following general formula

$$R_1\text{—}SO\text{—}R_2$$

wherein $R_1$ and $R_2$ individually represent alkyl containing 1–3 carbon atoms, and 2–10 wt % of linear alkane containing 10–55 carbon atoms, based on the total weight of the mixture in a sealed vessel with agitation to form a homogeneous fluid;
   b) pouring said homogeneous fluid into a mould having a desired shape;
   c) solidifying said homogeneous fluid in the mould by cooling;
   d) releasing the solidified fluid from the mould to form a medical catheter; and
   e) heat-treating the medical catheter from step d) and washing it with a polar organic solvent to remove sulfoxide.

2. A process of claim 1 wherein the molar percentage of vinyl alcohol unit of the polyvinyl alcohol is above 95% and the average degree of polymerization of the polyvinyl alcohol is in the range from about 500 to 20,000.

3. A process of claim 2 wherein the molar percentage of vinyl alcohol unit of the polyvinyl alcohol is above 99.5% and the average degree of polymerization of the polyvinyl alcohol is in the range from about 1,500 to 2,500.

4. A process of claim 1 wherein the sulfoxide is selected from the group consisting of dimethyl sulfoxide, diethyl sulfoxide, methyl ethyl sulfoxide and their mixture.

5. A process of claim 1 wherein the linear alkane having 10–55 carbon atoms is a petroleum wax.

6. A process of claim 5 wherein the petroleum wax is atoleine, paraffin, ozocerite or their mixtures.

7. A process claim 1 wherein the polar organic solvent is lower alcohol containing 1–4 carbon atoms, lower ketone containing 3 to 4 carbon atoms, their mixture, or their aqueous solution.

8. The process of claim 2 wherein the sulfoxide is selected from the group consisting of dimethyl sulfoxide, diethyl sulfoxide, methyl ethyl sulfoxide and their mixture.

9. The process of claim 3 wherein the sulfoxide is selected from the group consisting of dimethyl sulfoxide, diethyl sulfoxide, methyl ethyl sulfoxide and their mixture.

10. The process of claim 1 wherein in step a) the mixture is heated at a temperature of from 95° to 135° C. for 3 to 8 hours and thereafter is maintained at that temperature for 5 to 20 hours until a homogeneous fluid is formed.

11. The process of claim 1 wherein in step c) the fluid in the mould is cooled to 20° to 30° C.

12. The process of claim 1 wherein step e) is carried out by heating the catheter at a temperature of from 90° to 110° C.

13. The process of claim 12 wherein the heating is carded out for 15–45 minutes.

* * * * *

UNITED STATES PATENT AND TRADEMARK OFFICE
CERTIFICATE OF CORRECTION

PATENT NO.: 5,688,459
ISSUED: November 18, 1997
INVENTOR(S): Lijiang MAO, et al

It is certified that this error appears in the above-identified patent and that said Letters Patent is hereby corrected as shown below:

TITLE PAGE

[73]  should read: "Beijung" to read -- Beijing --.

Signed and Sealed this

Sixteenth Day of June, 1998

Attest:

BRUCE LEHMAN

Attesting Officer

Commissioner of Patents and Trademarks